(12) United States Patent
Duan et al.

(10) Patent No.: US 11,576,561 B2
(45) Date of Patent: Feb. 14, 2023

(54) CONTROL METHOD, CONTROL DEVICE, STORAGE MEDIUM, AND ELECTRONIC DEVICE FOR MAGNETIC CAPSULE

(71) Applicant: Ankon Medical Technologies (Shanghai) Co., LTD., Shanghai (CN)

(72) Inventors: Xiaodong Duan, Pleasanton, CA (US); Tingqi Wang, Wuxi (CN)

(73) Assignee: Ankon Medical Technologies (Shanghai) Co., LTD., Shanghai (CN)

( * ) Notice: Subject to any disclaimer, the term of this patent is extended or adjusted under 35 U.S.C. 154(b) by 111 days.

(21) Appl. No.: 16/988,695

(22) Filed: Aug. 9, 2020

(65) Prior Publication Data

US 2021/0068632 A1   Mar. 11, 2021

(30) Foreign Application Priority Data

Aug. 9, 2019 (CN) .......................... 201910743151.9

(51) Int. Cl.
   *A61B 1/00* (2006.01)
   *A61B 1/04* (2006.01)

(52) U.S. Cl.
   CPC ...... *A61B 1/00158* (2013.01); *A61B 1/00006* (2013.01); *A61B 1/00009* (2013.01); *A61B 1/041* (2013.01)

(58) Field of Classification Search
   CPC ............ A61B 1/00158; A61B 1/00006; A61B 1/00009
   See application file for complete search history.

(56) References Cited

U.S. PATENT DOCUMENTS

| | | | | |
|---|---|---|---|---|
| 5,319,442 A * | 6/1994 | Rosser | ................... | G01B 11/00 356/615 |
| 5,321,257 A * | 6/1994 | Danisch | ............... | G02B 6/2852 250/227.16 |
| 6,224,459 B1 * | 5/2001 | Stocker | ................... | B24B 49/02 451/6 |
| 7,319,781 B2 * | 1/2008 | Chen | ........................ | G06T 7/30 600/101 |
| 10,545,497 B1 * | 1/2020 | Cui | ...................... | G05D 1/0016 |
| 10,932,648 B2 * | 3/2021 | Mitsuhashi | ............... | A61B 1/00 |
| 2002/0087232 A1 * | 7/2002 | Lapham | ................. | B25J 9/1697 700/245 |
| 2004/0111011 A1 * | 6/2004 | Uchiyama | .............. | A61B 34/73 600/160 |

(Continued)

*Primary Examiner* — John P Leubecker
*Assistant Examiner* — Jae Woo
(74) *Attorney, Agent, or Firm* — Treasure IP Group, LLC (57) ABSTRACT

A control method, a control device, a storage medium, and an electronic device for a magnetic capsule endoscope is provided. The method includes: obtaining a safe operating range of a magnetic moving member to obtain a spatial range parameter, wherein the magnetic moving member controls the movement of the magnetic capsule endoscope through the movement of a magnetic field during movement; controlling a drive mechanism to drive the magnetic moving member to move within the safe operating range according to a specified movement mode according to the spatial range parameter, wherein the magnetic capsule endoscope moves under the attraction of the moving magnetic field of the magnetic moving part; and controlling the magnetic capsule endoscope to transmit captured videos or images during the movement.

8 Claims, 4 Drawing Sheets

(56) References Cited

U.S. PATENT DOCUMENTS

| | | | |
|---|---|---|---|
| 2004/0171915 A1* | 9/2004 | Glukhovsky | A61B 1/041 600/117 |
| 2006/0015012 A1* | 1/2006 | Sato | A61B 1/00006 600/117 |
| 2006/0119304 A1* | 6/2006 | Farritor | A61B 34/72 318/568.12 |
| 2006/0235275 A1* | 10/2006 | Rabinovitz | A61B 1/041 600/101 |
| 2006/0293565 A1* | 12/2006 | Uchimura | A61B 1/00121 600/179 |
| 2007/0221233 A1* | 9/2007 | Kawano | A61B 5/062 128/899 |
| 2007/0238987 A1* | 10/2007 | Minai | A61B 34/20 600/407 |
| 2007/0260139 A1* | 11/2007 | Minai | A61B 5/06 600/420 |
| 2008/0201016 A1* | 8/2008 | Finlay | B25J 9/1692 901/14 |
| 2009/0088634 A1* | 4/2009 | Zhao | B25J 9/1656 600/425 |
| 2010/0010305 A1* | 1/2010 | Kawano | A61B 1/0005 600/118 |
| 2010/0194992 A1* | 8/2010 | Kouno | G06F 16/70 348/700 |
| 2010/0298640 A1* | 11/2010 | Oneda | A61B 1/00105 600/109 |
| 2011/0196202 A1* | 8/2011 | Kimura | A61B 5/061 600/109 |
| 2011/0275893 A1* | 11/2011 | Kawano | A61B 1/00042 600/109 |
| 2011/0292196 A1* | 12/2011 | Kawano | A61B 34/73 348/E7.091 |
| 2012/0095289 A1* | 4/2012 | Kawano | A61B 1/00158 600/109 |
| 2012/0095290 A1* | 4/2012 | Kawano | A61B 1/00158 600/117 |
| 2012/0116162 A1* | 5/2012 | Kawano | A61B 34/73 600/118 |
| 2013/0110128 A1* | 5/2013 | Schostek | B25J 19/0008 606/130 |
| 2013/0303847 A1* | 11/2013 | Sitti | A61B 1/041 600/101 |
| 2014/0163357 A1* | 6/2014 | Higaki | G01S 5/14 600/424 |
| 2015/0313446 A1* | 11/2015 | Ogawa | A61B 1/00009 600/117 |
| 2016/0015473 A1* | 1/2016 | Frimer | A61B 1/00006 606/130 |
| 2016/0100771 A1* | 4/2016 | Chiba | A61B 5/062 600/424 |
| 2016/0143510 A1* | 5/2016 | Gotoh | A61B 1/00114 600/110 |
| 2016/0199147 A1* | 7/2016 | Shin | A61B 1/00194 600/411 |
| 2016/0213232 A1* | 7/2016 | Katayama | A61B 1/041 |
| 2016/0338573 A1* | 11/2016 | Aoki | A61B 1/00114 |
| 2016/0367121 A1* | 12/2016 | Kawano | A61B 1/041 |
| 2017/0020375 A1* | 1/2017 | Chiba | A61B 1/00158 |
| 2017/0032529 A1* | 2/2017 | De Villiers | G06T 7/73 |
| 2017/0035520 A1* | 2/2017 | Duan | A61B 17/0218 |
| 2017/0108356 A1* | 4/2017 | Iida | A61B 1/00158 |
| 2017/0150874 A1* | 6/2017 | Kawano | A61B 1/00158 |
| 2017/0156574 A1* | 6/2017 | Kawano | A61B 1/00 |
| 2017/0181661 A1* | 6/2017 | Chiba | A61B 1/041 |
| 2017/0224423 A1* | 8/2017 | Suzuki | A61B 5/065 |
| 2018/0008131 A1* | 1/2018 | Kawano | A61B 1/00158 |
| 2018/0256008 A1* | 9/2018 | Nishizawa | G06T 7/73 |
| 2018/0279852 A1* | 10/2018 | Rafii-Tari | A61B 5/0816 |
| 2019/0110839 A1* | 4/2019 | Rafii-Tari | A61B 34/20 |
| 2019/0145775 A1* | 5/2019 | Cui | G06F 16/29 701/446 |
| 2019/0307434 A1* | 10/2019 | Jones | A61B 5/036 |
| 2019/0387960 A1* | 12/2019 | Duan | A61B 34/73 |
| 2020/0100855 A1* | 4/2020 | Leparmentier | A61B 34/37 |
| 2020/0315721 A1* | 10/2020 | Rabindran | A61B 34/77 |

* cited by examiner

CONTROL METHOD, CONTROL DEVICE, STORAGE MEDIUM, AND ELECTRONIC DEVICE FOR MAGNETIC CAPSULE

CROSS-REFERENCE OF RELATED APPLICATIONS

The application claims priority to Chinese Patent Application No. 201910743151.9 filed on Aug. 9, 2019, the contents of which are incorporated by reference herein.

FIELD OF INVENTION

The present invention relates to a medical device and more particularly to a control method, a control device, a storage medium, and an electronic device for a magnetic capsule endoscope.

BACKGROUND

Capsule endoscopy has been used more and more clinically because of its features such as no intubation, good comfort, and no cross-infection. The capsule endoscopy examines digestive tract in detail, and the capsule endoscopy is controlled via an external control device.

However, in the process of clinical application and promotion of the capsule endoscope and the external control device, it often encounters problems such as difficulty in operation training and slow mastering of operations, and skilled operation skills require more experience to achieve. Without professional operators, it is difficult to apply the capsule endoscope and the external control device, especially in the areas and emergency rooms short of doctors.

No effective solution has been found for the above problems.

SUMMARY OF THE INVENTION

The present invention provides a control method, a control device, a storage medium, and an electronic device for a magnetic capsule endoscope to at least solve the technical problem of unsafe operation and incomplete scanning of the capsule endoscope during unskillful manual operation.

In an embodiment, a control method for magnetic capsule endoscope is provided. The control method comprises: obtaining a safe operating range of a magnetic moving member to obtain a spatial range parameter, wherein the magnetic moving member controls the movement of the magnetic capsule endoscope through the movement of a magnetic field during movement; controlling a drive mechanism to drive the magnetic moving member to move within the safe operating range according to a specified movement mode according to the spatial range parameter, wherein the magnetic capsule endoscope moves under the attraction of the moving magnetic field of the magnetic moving member; and controlling the magnetic capsule endoscope to transmit captured videos or images during the movement.

Further, the magnetic capsule endoscope moves in a subject; and before controlling the drive mechanism to drive the magnetic moving member to move within the safe operating range according to the specified movement mode, the method further comprises: obtaining a body type of the subject, and/or, a body position of the subject, and/or, an examined part of the subject; selecting a movement mode from a plurality of preset movement modes to obtain the specified movement mode according to the body type, and/or, the body position, and/or, the examined part, wherein each preset movement mode corresponds to a body type, and/or, a body position, and/or, an examined part.

Further, the spatial range parameter comprises an upper limit and/or a lower limit of the magnetic moving member in the direction of the vertical axis.

Further, in the specified movement mode, the movement of the magnetic capsule endoscope comprises rotation along the vertical axis and upward and downward movement in the direction of the vertical axis.

Further, obtaining the safe operating range of the magnetic moving member to obtain the spatial range parameter comprises: controlling the magnetic moving member to move to a lowest safe position in the direction of the vertical axis; receiving a first control instruction; in respond to the first control instruction, obtaining a vertical axis position parameter of the magnetic moving member in the lowest safety position and setting the vertical axis position parameter as the lower limit of the spatial range parameter; and/or, controlling the magnetic moving member to move to a highest safe position in the direction of the vertical axis; receiving a first control instruction; in respond to the first control instruction, obtaining a vertical axis position parameter of the magnetic moving member in the highest safety position and setting the vertical axis position parameter as the upper limit of the spatial range parameter.

Further, after receiving the first control instruction, the method further comprises: receiving a second control instruction; in respond to the second control instruction, releasing the upper limit and/or the lower limit.

Further, after controlling the magnetic capsule endoscope to transmit the captured videos or images during the movement, the method further comprises: obtaining an image frame labeled by a user in the video or image; searching for the position information of the magnetic moving member corresponding to the image frame; moving the magnetic moving member to a corresponding position according to the position information; and controlling the magnetic capsule endoscope to capture images within the preset range near the corresponding position.

In another embodiment, a control device for magnetic capsule endoscope is provided. The control device comprising: an collection module, for obtaining a safe operating range of a magnetic moving member to obtain a spatial range parameter, wherein the magnetic moving member controls the movement of the magnetic capsule endoscope through the movement of a magnetic field during movement; a first control module, for controlling a drive mechanism to drive the magnetic moving member to move within the safe operating range according to a specified movement mode according to the spatial range parameter, wherein the magnetic capsule endoscope moves under the attraction of the moving magnetic field of the magnetic moving member; and a second control module, for controlling the magnetic capsule endoscope to transmit captured videos or images during the movement.

In still another embodiment, a storage medium is also provided. The storage medium stores computer programs and the computer programs are set to execute the steps in any of the above embodiments.

In still another embodiment, an electronic device is also provided comprising a memory and a processor, where the memory stores computer programs and the processor is set to run the computer programs to execute the steps in any of the above methods.

According to the embodiments, the present invention obtains the safe operating range of the magnetic moving member to obtain the spatial range parameter, wherein the magnetic moving member controls the movement of the magnetic capsule endoscope through the movement of a magnetic field during movement. The present invention further controls the drive mechanism to drive the magnetic moving member to move within the safe operating range according to the specified movement mode according to the spatial range parameter, so that the magnetic capsule endoscope moves under the attraction of the moving magnetic field of the magnetic moving member. The present invention further controls the magnetic capsule endoscope to transmit captured videos or images during the movement. It solves the technical problem of unsafe operation and incomplete scanning of the capsule endoscope during unskillful manual operation, and it achieves a technical effect of safe and efficient control of the capsule endoscope scanning.

BRIEF DESCRIPTION OF THE DRAWINGS

The accompanying drawings here provide a further understanding of the present invention and are incorporated in and constitute a part of the present invention. The schematic embodiments of the present invention and their descriptions are used to explain the invention and do not constitute undue limitations on the present invention.

DETAILED DESCRIPTION

In order to enable those skilled in the art to better understand the application, the present invention can be described in detail below with reference to the accompanying drawings and preferred embodiments. However, the embodiments are not intended to limit the invention, and obviously, the described embodiments are only a part of the embodiments of the present invention, but not all of them. In the absence of conflict, the embodiments of the present invention and the features in the embodiments can be combined with each other. All other embodiments obtained by those having ordinary skill in the art without creative work based on the embodiments of the present invention are included in the scope of the present invention.

It should be noted that the terms, such as "first" and "second", as described in the specification and claims of the present invention and the accompanying drawings are used only to distinguish similar objects but do not necessarily describe a particular sequence or order. It should be understood that the terms used in this way are interchangeable where appropriate, so that the embodiments of the present invention described herein can be performed in a sequence other than those diagrammed or described herein. In addition, the terms such as "comprise", "include" and "have" and any of their variants are intended to cover non-exclusive inclusions. For example, for a process, a method, a system, a product or a device that comprises a series of steps or units, it is not necessarily limited to list all the steps or units, but other unlisted or inherent steps or units can also be included in such process, method, product or device.

Embodiment 1

This embodiment provides a control method for a magnetic capsule endoscope. The control method can run in an industrial personal computer (IPC), a mobile terminal, a hand-held terminal or other similar computing devices. Running in different computing devices only means a difference in execution body. The person skilled in the art can foresee that the same technical effect can be produced though running in different operation devices.

Figure 1:
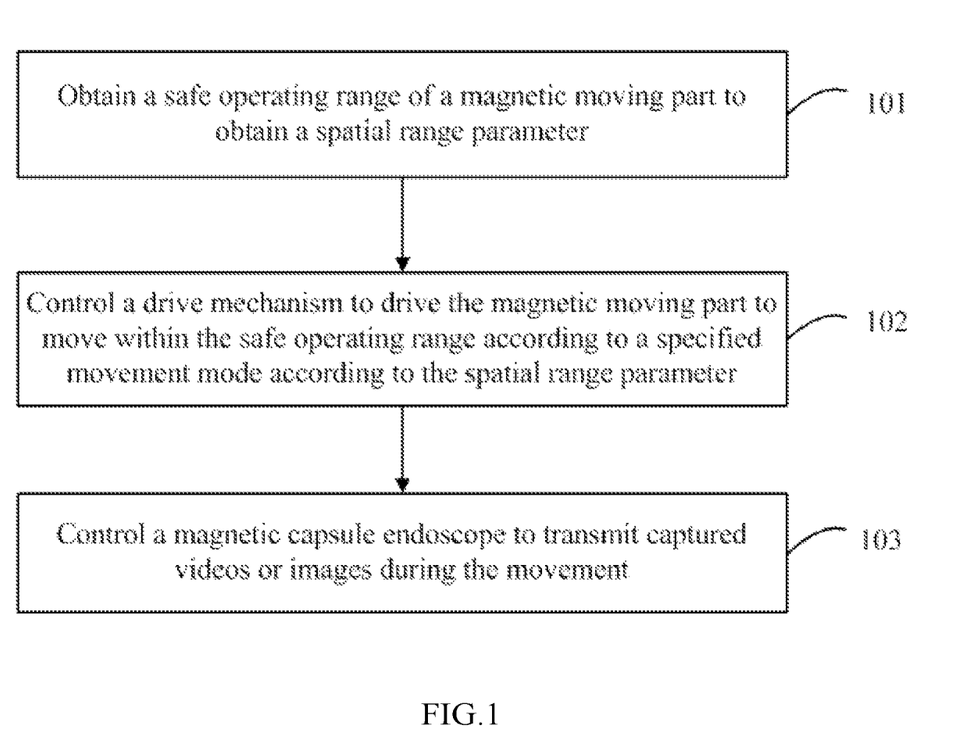
FIG. 1 shows a flowchart of a control method for a magnetic capsule endoscope according to an embodiment of the present invention.

The control method for the magnetic capsule endoscope provided in this embodiment, as shown in FIG. 1, comprises the following steps:

Step 101: obtaining a safe operating range of the magnetic moving member to obtain a spatial range parameter, wherein the magnetic moving member is used to control the movement of the magnetic capsule endoscope through the movement of a magnetic field during movement.

The magnetic moving member is a component that generates the magnetic field and can generate three-dimensional translational movement and rotational movement driven by a drive mechanism. When the magnetic moving member moves, the magnetic field generated moves too, which causes changes in the spatial range and the maximum magnetic force position of the magnetic field, and thus attracts the magnetic capsule endoscope in the magnetic field to move with the movement of the magnetic moving member. The magnetic capsule endoscope can move in a non-magnetic cavity, e.g. the stomach of a subject, etc.

In order to prevent safety accidents such as collision to or extrusion to the subject, or causing the magnetic capsule endoscope controlled by the magnetic moving member to move to the outside of the non-magnetic cavity when the magnetic moving member is moving, it is necessary to set a safe operating range. The safe operating range can be a range in a three-dimensional spatial coordinate system, an area defined by the maximum plane and/or the minimum plane of the x-axis and/or y-axis and/or z-axis.

In this embodiment, since the subject is lying on an examination bed in a supine position or a lateral position, the safe operating range can be set as the highest position and the lowest position on the z-axis, that is, the spatial range parameters comprises the upper limit and/or the lower limit on the vertical axis (z-axis).

It is necessary to ensure that the magnetic capsule endoscope does not exceed the body part to be examined such as fundus of the stomach (upper stomach) when the magnetic moving member is at the highest position on the vertical axis; and ensure that the magnetic capsule endoscope does not exceed the body part to be examined such as antrum (lower stomach) and not touch the subject when the magnetic moving member is at the lowest position on the vertical axis.

An optional specific method of setting the lower limit comprises the following steps:

Step 11: controlling the magnetic moving member to move to the lowest safe position in the direction of the vertical axis. The control mode can be manually adjusted by an IPC or a remote control system that can control the drive mechanism, and move the magnetic moving member down the vertical axis to the lowest position without touching the subject.

Step 12: receiving a first control instruction. The first control instruction is used to give an instruction to obtain and set the parameter of the lower limit. The first control instruction can be received through a console panel of the IPC or a console panel of the remote control system.

Step 13: responding to the first control instruction, obtaining the vertical axis position parameter of the magnetic moving member at the lowest safety position and setting the vertical axis position parameter as the lower limit of the spatial range parameter.

The step of setting the upper limit is similar to that of setting the lower limit, which is: controlling the magnetic moving member to move to the highest safe position in the direction of the vertical axis, and ensuring that the magnetic capsule endoscope does not exceed the body part to be examined when the magnetic moving member is at the highest position on the vertical axis; receiving a first control instruction that is used to give an instruction to obtain and set the parameter of the upper limit; and responding to the first control instruction, obtaining the vertical axis position parameter of the magnetic moving member at the highest safety position and setting the vertical axis position parameter as the upper limit of the spatial range parameter.

Further, after receiving the first control instruction, if a second control instruction is received, the set upper limit and/or lower limit are released.

Step 102: according to the spatial range parameter, controlling the drive mechanism to drive the magnetic moving member to move within the safe operating range according to a specified movement mode, so that the magnetic capsule endoscope moves under the attraction of the moving magnetic field of the magnetic moving member.

When the magnetic capsule endoscope is used to move inside the subject, a movement mode is selected from a plurality of preset movement modes to obtain the specified movement mode according to the body type (e.g. medium and large, small, etc.), and/or the type of body position (e.g. the supine position, supine, a left lateral position, a right lateral position, the prone position, etc.), and/or the examined part (e.g., stomach, large intestine, or different parts of the stomach such as fundus, antrum, etc.). Each preset movement mode corresponds a body type, and/or, a type of body position, and/or, an examined part.

For example, when the stomach is examined, different movement modes are set for a medium and large body type and a small sized body type to meet the movement range for the stomach of different body types. Different movement modes are set for the supine position, the left lateral position, the right lateral position, and the prone position to meet the different movement paths for the stomach in different body positions.

Figure 2:
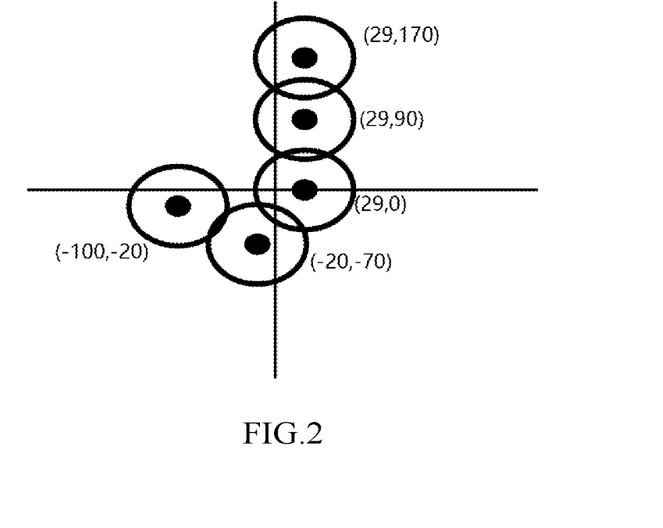
FIG. 2 shows a schematic diagram of fixed positions for scanning the stomach of a subject in a supine position of a medium and large body.

FIG. 2 shows a schematic diagram of fixed positions for scanning the stomach of a subject in a supine position of a medium and large body. FIG. 2 is a top view of an xy-axis plane, the horizontal axis is the x-axis and the vertical axis is the y-axis. The two-dimensional coordinate points shown in FIG. 2 are the absolute coordinate positions for fixed position scanning, where the fixed position scanning is done in a way of automatically scanning up and down along the z-axis.

Figure 3:
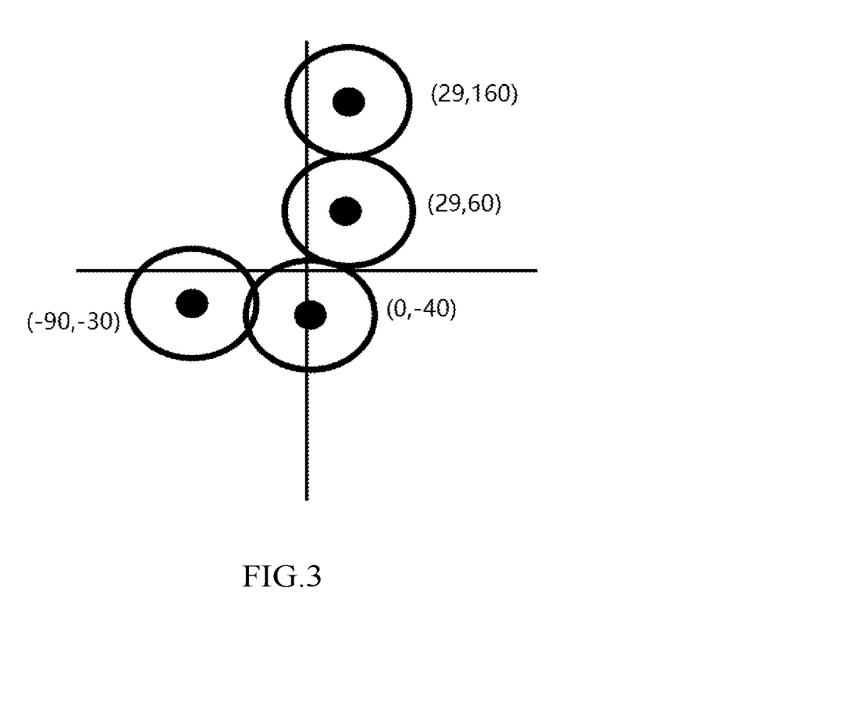
FIG. 3 shows a schematic diagram of fixed positions for scanning the stomach of a small sized body in a supine position.

FIG. 3 shows a schematic diagram of fixed positions for scanning the stomach of a small-sized body in a supine position. FIG. 3 is a top view of an xy-axis plane, the horizontal axis is the x-axis and the vertical axis is the y-axis. The two-dimensional coordinate points shown in FIG. 3 are the absolute coordinate positions for fixed position scanning From the contrast between FIG. 2 and FIG. 3, the stomach of a small sized body requires less points for fixed position scanning.

Figure 4:
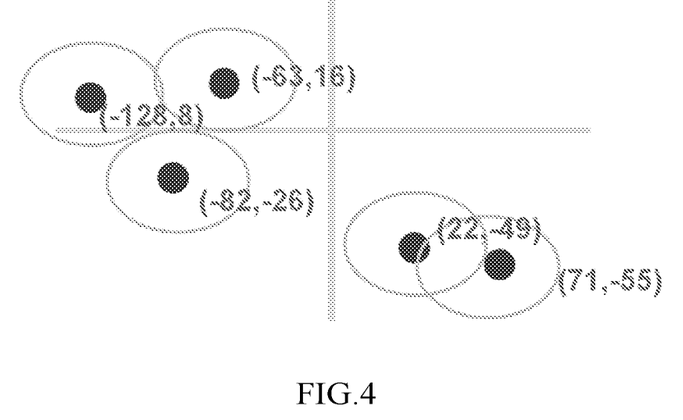
FIG. 4 shows a schematic diagram of fixed positions for scanning the stomach of a subject in a prone position of a medium and large body.

FIG. 4 shows a schematic diagram of fixed positions for scanning the stomach of a subject in a prone position of a medium and large body. FIG. 4 is a top view of an xy-axis plane, the horizontal axis is the x-axis and the vertical axis is the y-axis. The two-dimensional coordinate points shown in FIG. 4 are the absolute coordinate positions for fixed position scanning From the contrast between FIG. 2 and FIG. 4, the distribution of the fixed positions for a supine body position is different from that for a prone body position, which means the scanning paths are different.

For example, when the stomach is examined, different movement modes are set for different examined parts (e.g. fundus or antrum) to determine the movement range for different examined parts. Different movement modes are set for the supine position, the left lateral position, the right lateral position, and the prone position to meet the different movement paths for the examined parts in different body positions.

A specific application scenario is scanning the fundus of a subject lying in a left lateral position. In this application scenario, the specific process of the above embodiment is: first, according to the preset coordinate values of the fundus in a left lateral position, positioning the capsule to the fundus area, and controlling the capsule to move to the upper limit of the fundus area on the z-axis; then, controlling the capsule to be placed horizontally along the horizontal axis and to rotate 360 degrees horizontally; and then controlling the end of the capsule installed with a camera to face upwards, and controlling the magnetic moving member to rotate 45 degrees along the horizontal axis, so that the upper end of the capsule is flipped down 45 degrees vertically; finally, controlling the capsule to rotate 360 degrees horizontally, so that the camera of the capsule can capture images of the fundus.

Step 103: controlling the magnetic capsule endoscope to transmit the captured videos or images during the movement.

The magnetic capsule endoscope can capture an image at each rotation angle or at every fixed time period (such as 0.5 s). The magnetic capsule endoscope can also capture images at a fixed frequency.

Optionally, in order to further scan a fixed position after controlling the magnetic capsule endoscope to transmit the captured videos or images during the movement, the method may further comprise the following steps:

Step 21: obtaining an image frame labeled by a user in the video or image;

Step 22: searching for the position information of the magnetic moving member corresponding to the image frame;

Step 23: moving the magnetic moving member to a corresponding position according to the position information;

Step 24: controlling the magnetic capsule endoscope to capture images within a preset range near the corresponding position.

A specific application scenario is that the body position is the supine position, which means that the subject is lying on his/her back on the examination bed, and it is needed to exam and scan (fixed position scanning) the fixed position up and down on the xy-axis plane (based on the position information of the labeled image frame). In this application scenario, the specific process of the above embodiment is: first, searching for the position where the capsule is in and controlling the capsule to move to the fixed position and move to the upper limit of the fixed point on the z-axis; then, controlling the end of the capsule installed with a camera to face upwards, and controlling the magnetic moving member to rotate 45 degrees along the horizontal axis, so that the upper end of the capsule is flipped 45 degrees vertically; finally, controlling the capsule to rotate 360 degrees horizontally, so that the camera of the capsule can capture images of the upper and top of the cavity at the fixed position; further, controlling the capsule to move along the vertical axis to the lowest position (lower limit) of the z-axis, and controlling the end of the capsule installed with a camera to face down; and then controlling the magnetic moving member to rotate 45 degrees along the horizontal axis, so that the lower end of the capsule is flipped up 45 degrees vertically; finally, controlling the capsule to rotate 360 degrees horizontally, so that the camera of the capsule can capture images of the lower and bottom of the cavity at the fixed point.

Obtaining the safe operating range of the magnetic moving member and controlling the drive mechanism to drive the magnetic moving member to move within the safe operating range according to the specified movement mode, the embodiment of the present invention enables the magnetic capsule endoscope to move safely and reliably and to capture all-round videos or images of the interior of the cavity, achieving a safe and efficient operation.

It should be noted that the steps shown in the drawing can be performed on a computer system with a set of instructions that can be executed in a computer. Furthermore, although the logical sequence is shown in the flow chart, in some cases the steps shown or described here can be performed in a different sequence.

Through the above description of the embodiment, the person skilled in the art can clearly understand that the method in above embodiment can be implemented based on software and necessary general-purpose hardware platform, or only based on hardware, but in many cases the former is a better way. Based on this understanding, the technical solution of the present invention essentially or the part that contributes to prior art is implemented in the form of a software product. The software product is stored in a storage medium (such as a ROM/RAM, a diskette, a CD), and comprises a plurality of instructions to instruct a terminal device (a mobile phone, a computer, a server, or a network equipment, etc.) to execute the method described in each embodiment of the present invention.

Embodiment 2

In this embodiment, a control device for the magnetic capsule endoscope is also provided. The control device is used to implement the above-mentioned embodiment 1 and its preferred embodiments. For terms or implementations not detailed in this embodiment, refer to the relevant descriptions in embodiment 1, and the descriptions that have been described cannot be repeated.

The term "module" used hereafter refers to as a combination of software and/or hardware that can implement preset functions. Although the device described in the following embodiments is preferably implemented by software, the implementation by hardware or a combination of software and hardware can also be conceived.

Figure 5:
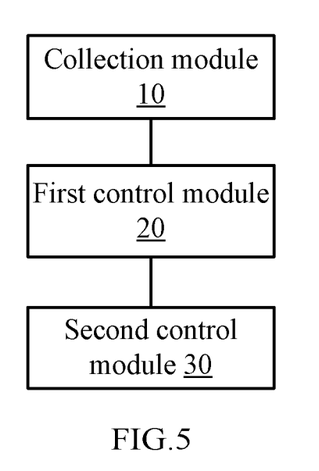
FIG. 5 shows a schematic diagram of a control device for the magnetic capsule endoscope according to an embodiment of the present invention.

FIG. 5 shows a schematic diagram of a control device for the magnetic capsule endoscope according to an embodiment of the present invention. As shown in FIG. 5, the control device comprises a collection module 10, a first control module 20 and a second control module 30.

The collection module 10 is used to obtain the safe operating range of the magnetic moving member to obtain the spatial range parameter, wherein the magnetic moving member is used to control the movement of the magnetic capsule endoscope through the movement of the magnetic field during movement. The first control module 20 is used to control the drive mechanism to drive the magnetic moving member to move within the safe operating range according to a specified movement mode according to the spatial range parameter, so that the magnetic capsule endoscope moves under the attraction of the moving magnetic field of the magnetic moving member. The second control module 30 is used to control the magnetic capsule endoscope to transmit captured videos or images during the movement.

In an optional embodiment, the magnetic capsule endoscope is used to move in the subject. Before controlling the drive mechanism to drive the magnetic moving member to move within the safe operating range according to the specified movement mode, the collection module 10 is further used to obtain the body type of a subject, and/or, the body position of the subject, and/or, the examined part of the subject. The control device further comprises a selection module for selecting a movement mode from a plurality of preset movement modes according to the body type, and/or, the body position, and/or, the examined part, to obtain the specified movement mode. Each preset movement mode corresponds to a body type, and/or, a body position, and/or, an examined part.

In an optional embodiment, the spatial range parameter comprises the upper limit and/or the lower limit of the magnetic moving member in the direction of the vertical axis.

In an optional embodiment, in the specified movement mode, the movement of the magnetic capsule endoscope comprises rotation along the vertical axis and upward and downward movement in the direction of the vertical axis.

In an optional embodiment, the collection module comprises: a first control unit used to control the magnetic moving member to move to the lowest safe position in the direction of the vertical axis; a first receiving unit used to receive a first control instruction; a first collection unit used to respond to the first control instruction to obtain the vertical axis position parameter of the magnetic moving member at the lowest safety position and set the vertical axis position parameter as the lower limit of the spatial range parameter.

In an optional embodiment, the collection module comprises: a second control unit used to control the magnetic moving member to move to the highest safe position in the direction of the vertical axis; a second receiving unit used to receive a first control instruction; a second collection unit used to respond to the first control instruction to obtain the vertical axis position parameter of the magnetic moving member in the highest safety position and set the vertical axis position parameter as the upper limit of the spatial range parameter.

In an optional embodiment, the control device further comprises: a receive module used to receive the second control instruction after receiving the first control instruction; a release module used to respond to the second control instruction to release the upper limit and/or the lower limit.

In an optional embodiment, the collection module is further used to obtain an image frame labeled by a user in the video or image after controlling the magnetic capsule endoscope to transmit the captured videos or images during the movement. The control device further comprises: a search module used to search for the position information of the magnetic moving member corresponding to the image frame; a movement module used to move the magnetic moving member to a corresponding position according to the corresponding position information; and a third control module used to control the magnetic capsule endoscope to capture images within the preset range near the corresponding position.

It should be noted that each of the above modules can be implemented by software or hardware. In terms of implementation by hardware, the implementation method comprises, but not limited to: the above modules are all arranged in the same processor, or the above modules are arranged in different processors in the form of arbitrary combination.

Obviously, the person skilled in the art understand that the modules or steps of the present invention can be implemented with a common computing device, and specifically, the modules or steps can be integrated on a single computing device or distribute on a network of a plurality of computing devices. Alternatively, the modules or steps can be implemented with the program code that can be executed on the computing device, so that they can be stored in the storage device for the computing device to execute. In some cases, the steps shown or described herein can be implemented in a different sequence. Or, they can be made into individual integrated circuit modules, or some of them can be made into a single integrated circuit module for implementation. In this way, the present invention is not limited to any specific combinations of hardware and software.

Embodiment 3

In this embodiment, a storage medium is also provided. The storage medium stores computer programs and the computer programs are set to execute the steps in any of the above embodiments.

Alternatively, the above storage medium provided in the embodiment of the present invention may include, but not limited to a medium that can store computer programs, such as a USB flash drive, a Read-Only Memory (ROM), a Random Access Memory (RAM), a mobile hard disk, a diskette, a CD, etc.

Embodiment 4

In this embodiment, an electronic device is also provided, comprising a memory and a processor, where the memory stores computer programs and the processor is set to run the computer programs to execute the steps in any of the above embodiments.

Alternatively, the electronic device may also comprise a transmission device and an input and output device, wherein the transmission device is connected to the processor, and the input and output device is connected to the processor.

The person skilled in the art realizes that the present invention by no means is limited to the preferred embodiments described above. On the contrary, many modifications and variations are possible within the scope of the appended claims. Any modifications, equivalent substitutions, improvements, etc. made within the principles of the present invention are intended to be included within the scope of the present invention.

What is claimed is:

1. A control method for a magnetic capsule endoscope, comprising:

obtaining a safe operating range of a magnetic moving member to obtain a spatial range parameter, wherein the magnetic moving member controls the movement of the magnetic capsule endoscope through the movement of a magnetic field during movement of the magnetic moving member, wherein safe is defined as being within physical mechanical limits of an external controlling robotic device;

controlling a drive mechanism to drive the magnetic moving member to move within the safe operating range according to a specified movement mode according to the spatial range parameter, wherein the magnetic capsule endoscope moves under the attraction of the moving magnetic field of the magnetic moving member; and controlling the magnetic capsule endoscope to transmit captured videos or images during the movement of the capsule, obtaining an image frame labeled by a user in the video or image;

searching for the position information of the magnetic moving member corresponding to the image frame;

moving the magnetic moving member to a corresponding position according to the position information; and controlling the magnetic capsule endoscope to capture images within the preset range near the corresponding position.

2. The method of claim 1, wherein the magnetic capsule endoscope moves in a subject; and wherein before controlling the drive mechanism to drive the magnetic moving member to move within the safe operating range according to the specified movement mode, the method further comprises:

obtaining a body type of the subject, and/or, a body position of the subject, and/or, an examined part of the subject;

selecting a movement mode from a plurality of preset movement modes to obtain the specified movement mode according to the body type, and/or, the body position, and/or, the examined part, wherein each preset movement mode corresponds to a body type, and/or, a body position, and/or, an examined part.

3. The method of claim 1, wherein the spatial range parameter comprises an upper limit and/or a lower limit of the magnetic moving member in the direction of the vertical axis.

4. The method of claim 3, wherein in the specified movement mode, the movement of the magnetic capsule endoscope comprises rotation along the vertical axis and upward and downward movement in the direction of the vertical axis.

5. The method of claim 3, wherein obtaining the safe operating range of the magnetic moving member to obtain the spatial range parameter comprises:

controlling the magnetic moving member to move to a lowest safe position in the direction of the vertical axis; receiving a first control instruction; in response to the first control instruction, obtaining a vertical axis position parameter of the magnetic moving member in the lowest safe position and setting the vertical axis position parameter as the lower limit of the spatial range parameter; and/or, controlling the magnetic moving member to move to a highest safe position in the direction of the vertical axis; receiving a first control instruction; in response to the first control instruction, obtaining a vertical axis position parameter of the magnetic moving member in the highest safe position and setting the vertical axis position parameter as the upper limit of the spatial range parameter.

6. The method of claim 5, wherein after receiving the first control instruction, the method further comprises:
   receiving a second control instruction;
   in response to the second control instruction, releasing the upper limit and/or the lower limit.

7. The method of claim 1, wherein the control method is performed by a control device, comprising: one or more processors, configured to,
   obtain a safe operating range of a magnetic moving member to obtain a spatial range parameter, wherein the magnetic moving member controls the movement of the magnetic capsule endoscope through the movement of a magnetic field during movement of the magnetic moving member;
   control a drive mechanism to drive the magnetic moving member to move within the safe operating range according to a specified movement mode according to the spatial range parameter, wherein the magnetic capsule endoscope moves under the attraction of the moving magnetic field of the magnetic moving member; and
   control the magnetic capsule endoscope to transmit captured videos or images during the movement of the capsule.

8. The method of claim 1, wherein the control method is performed by a control system having a storage medium, wherein the storage medium stores computer programs, the computer programs are set to execute a control method for a magnetic capsule endoscope,
   wherein the method comprises:
   obtaining a safe operating range of a magnetic moving member to obtain a spatial range parameter, wherein the magnetic moving member controls the movement of the magnetic capsule endoscope through the movement of a magnetic field during movement of the magnetic moving member;
   controlling a drive mechanism to drive the magnetic moving member to move within the safe operating range according to a specified movement mode according to the spatial range parameter, wherein the magnetic capsule endoscope moves under the attraction of the moving magnetic field of the magnetic moving member; and
   controlling the magnetic capsule endoscope to transmit captured videos or images during the movement of the capsule.

* * * * *